United States Patent
Zhou et al.

(10) Patent No.: US 10,837,036 B2
(45) Date of Patent: Nov. 17, 2020

(54) METHOD FOR PREPARING L-ASPARTIC ACID WITH MALEIC ACID BY WHOLE-CELL BIOCATALYSIS

(71) Applicant: JIANGNAN UNIVERSITY, Wuxi (CN)

(72) Inventors: Zhemin Zhou, Wuxi (CN); Long Yu, Wuxi (CN); Li Zhou, Wuxi (CN); Wenjing Cui, Wuxi (CN); Zhongmei Liu, Wuxi (CN); Junling Guo, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 117 days.

(21) Appl. No.: 16/310,443

(22) PCT Filed: Jan. 26, 2018

(86) PCT No.: PCT/CN2018/074337
§ 371 (c)(1),
(2) Date: Dec. 16, 2018

(87) PCT Pub. No.: WO2019/119614
PCT Pub. Date: Jun. 27, 2019

(65) Prior Publication Data
US 2020/0255875 A1    Aug. 13, 2020

(30) Foreign Application Priority Data
Dec. 19, 2017    (CN) .......................... 2017 1 1374147

(51) Int. Cl.
*C12N 9/88*    (2006.01)
*C12N 9/90*    (2006.01)
*C12P 13/20*    (2006.01)

(52) U.S. Cl.
CPC ................ *C12P 13/20* (2013.01); *C12N 9/88* (2013.01); *C12N 9/90* (2013.01); *C12Y 403/01001* (2013.01); *C12Y 502/01001* (2013.01)

(58) Field of Classification Search
CPC .... C12N 1/10; C12N 9/90; C12N 9/88; C12P 13/20; C12Y 502/01001; C12Y 403/01001
See application file for complete search history.

(56) References Cited

U.S. PATENT DOCUMENTS

| | | | |
|---|---|---|---|
| 3,391,059 A * | 7/1968 | Takamura | C12P 13/20 435/109 |
| 6,280,980 B1 * | 8/2001 | Waller | C12P 13/20 435/109 |

FOREIGN PATENT DOCUMENTS

| | | |
|---|---|---|
| CN | 106222122 A | 12/2016 |
| CN | 106636052 A | 5/2017 |
| CN | 108103120 A | 6/2018 |
| JP | 2000139466 A | 5/2000 |

\* cited by examiner

*Primary Examiner* — Karen Cochrane Carlson
(74) *Attorney, Agent, or Firm* — SZDC Law P.C.

(57) ABSTRACT

The invention relates to the technical field of bioengineering, and discloses a method for synthesizing L-aspartic acid with maleic acid by whole-cell biocatalysis. In the invention, a recombinant strain co-expressing maleate cis-trans isomerase and L-aspartate lyase is constructed, and engineered and optimized to produce L-aspartic acid from maleic acid with a high conversion rate by whole-cell catalyzing. Relatively inexpensive maleic acid is utilized by the recombinant strain to produce L-aspartic acid, where maleic acid is reacted completely in 40-120 min, there is almost no buildup of the intermediate fumaric acid, and the conversion rate is up to 98% or more.

12 Claims, 5 Drawing Sheets
Specification includes a Sequence Listing.

SEQUENCE LISTING

```
<160> NUMBER OF SEQ ID NOS: 25

<210> SEQ ID NO 1
<211> LENGTH: 250
<212> TYPE: PRT
<213> ORGANISM: Serratia marcescens
<220> FEATURE:
<223> OTHER INFORMATION: isomerase sequence

<400> SEQUENCE: 1

Met Ser Asn His Tyr Arg Ile Gly Gln Ile Val Pro Ser Ser Asn Thr
1               5                   10                  15

Thr Met Glu Thr Glu Ile Pro Ala Met Leu Gly Ala Arg Gln Leu Ile
            20                  25                  30

Arg Pro Glu Arg Phe Thr Phe His Ser Ser Arg Met Arg Met Lys His
        35                  40                  45

Val Asn Lys Glu Glu Leu Ala Ala Met Asp Ala Glu Ser Asp Arg Cys
    50                  55                  60

Ala Leu Glu Leu Ser Asp Ala Arg Val Asp Val Leu Gly Tyr Ala Cys
65                  70                  75                  80

Leu Val Ala Ile Met Ala Met Gly Leu Gly Tyr His Arg Glu Ser Gln
                85                  90                  95

Ala Arg Leu Ala Gln Val Thr Lys Asp Asn Gln Ala Ala Ala Pro Val
            100                 105                 110

Ile Ser Ser Ala Gly Ala Leu Val Asn Gly Leu Lys Val Ile Gly Ala
        115                 120                 125

Lys Arg Ile Ala Leu Val Ala Pro Tyr Met Lys Pro Leu Thr Gln Leu
    130                 135                 140

Val Val Asp Tyr Ile Gln His Glu Gly Ile Glu Val Lys Val Trp Arg
145                 150                 155                 160

Ala Leu Glu Ile Pro Asp Asn Leu Asp Val Gly Arg His Asp Pro Ala
                165                 170                 175

Arg Leu Pro Gly Ile Val Ala Glu Met Asp Leu Arg Glu Val Asp Ala
            180                 185                 190

Ile Val Leu Ser Ala Cys Val Gln Met Pro Ser Leu Pro Ala Val Pro
        195                 200                 205

Thr Val Glu Ala Gln Thr Gly Lys Pro Val Ile Thr Ala Ala Ile Ala
    210                 215                 220

Thr Thr Tyr Ala Met Leu Thr Ala Leu Glu Leu Glu Pro Ile Val Pro
225                 230                 235                 240

Gly Ala Gly Ala Leu Leu Ser Gly Ala Tyr
                245                 250

<210> SEQ ID NO 2
<211> LENGTH: 753
<212> TYPE: DNA
```

<213> ORGANISM: Serratia marcescens
<220> FEATURE:
<223> OTHER INFORMATION: isomerase sequence

<400> SEQUENCE: 2

```
atgagcaacc actaccgcat cggccagatc gtgcccagct ccaacaccac gatggaaacc    60
gagatcccgg cgatgctggg cgcgcgccag ctgatacgcc cggagcgttt caccttcac   120
tccagccgca tgcgcatgaa acacgtcaat aaagaagaat ggcggcgat ggacgccgag   180
tccgatcgct gcgcgctgga gctgtccgac gcgcgggtcg acgtgctcgg ctacgcctgc   240
ctggtggcca tcatggcgat ggggctgggc taccaccgcg aatcgcaggc ccggctggcg   300
caggtgacga agacaatca ggccgccgcg ccggtcatca gcagcgccgg cgcgctggtc   360
aacggcctga aggtgatcgg cgccaaacgc atcgcgctgg tggcgcccta catgaaaccg   420
ctgacccagc tggtggtgga ctacatccag cacgaaggca tcgaggtcaa ggtatggcgc   480
gcgctggaga tcccggacaa cctcgacgtc ggccggcacg atccggccag ctgccggggg   540
atcgtcgccg agatggactt acgcgaggtc gatgctatcg tgctgtccgc ctgcgtgcag   600
atgccttcgc tgccggccgt cccgacggtg gaggcccaaa ccggcaaacc ggtgatcacc   660
gccgccatcg ccaccactta cgcgatgctg accgcgctgg agctggaacc gatcgttccc   720
ggcgccggcg ccctgctgtc cggcgcttat tga                               753
```

<210> SEQ ID NO 3
<211> LENGTH: 478
<212> TYPE: PRT
<213> ORGANISM: Escherichia coli
<220> FEATURE:
<223> OTHER INFORMATION: L-aspartate lyase sequence

<400> SEQUENCE: 3

```
Met Ser Asn Asn Ile Arg Ile Glu Glu Asp Leu Leu Gly Thr Arg Glu
1               5                  10                  15

Val Pro Ala Asp Ala Tyr Tyr Gly Val His Thr Leu Arg Ala Ile Val
            20                  25                  30

Asn Phe Tyr Ile Ser Asn Asn Lys Ile Ser Asp Ile Pro Glu Phe Val
        35                  40                  45

Arg Gly Met Val Met Val Lys Lys Ala Ala Ala Met Ala Asn Lys Glu
    50                  55                  60

Leu Gln Thr Ile Pro Lys Ser Val Ala Asn Ala Ile Ile Ala Ala Cys
65                  70                  75                  80

Asp Glu Val Leu Asn Asn Gly Lys Cys Met Asp Gln Phe Pro Val Asp
                85                  90                  95

Val Tyr Gln Gly Gly Ala Gly Thr Ser Val Asn Met Asn Thr Asn Glu
            100                 105                 110

Val Leu Ala Asn Ile Gly Leu Glu Leu Met Gly His Gln Lys Gly Glu
        115                 120                 125

Tyr Gln Tyr Leu Asn Pro Asn Asp His Val Asn Lys Cys Gln Ser Thr
    130                 135                 140

Asn Asp Ala Tyr Pro Thr Gly Phe Arg Ile Ala Val Tyr Ser Ser Leu
145                 150                 155                 160

Ile Lys Leu Val Asp Ala Ile Asn Gln Leu Arg Glu Gly Phe Glu Arg
                165                 170                 175

Lys Ala Val Glu Phe Gln Asp Ile Leu Lys Met Gly Arg Thr Gln Leu
            180                 185                 190

Gln Asp Ala Val Pro Met Thr Leu Gly Gln Glu Phe Arg Ala Phe Ser
```

```
                195                 200                 205
Ile Leu Leu Lys Glu Glu Val Lys Asn Ile Gln Arg Thr Ala Glu Leu
    210                 215                 220

Leu Leu Glu Val Asn Leu Gly Ala Thr Ala Ile Gly Thr Gly Leu Asn
225                 230                 235                 240

Thr Pro Lys Glu Tyr Ser Pro Leu Ala Val Lys Lys Leu Ala Glu Val
                245                 250                 255

Thr Gly Phe Pro Cys Val Pro Ala Glu Asp Leu Ile Glu Ala Thr Ser
                260                 265                 270

Asp Cys Gly Ala Tyr Val Met Val His Gly Ala Leu Lys Arg Leu Ala
                275                 280                 285

Val Lys Met Ser Lys Ile Cys Asn Asp Leu Arg Leu Leu Ser Ser Gly
    290                 295                 300

Pro Arg Ala Gly Leu Asn Glu Ile Asn Leu Pro Glu Leu Gln Ala Gly
305                 310                 315                 320

Ser Ser Ile Met Pro Ala Lys Val Asn Pro Val Val Pro Glu Val Val
                325                 330                 335

Asn Gln Val Cys Phe Lys Val Ile Gly Asn Asp Thr Val Thr Met
                340                 345                 350

Ala Ala Glu Ala Gly Gln Leu Gln Leu Asn Val Met Glu Pro Val Ile
    355                 360                 365

Gly Gln Ala Met Phe Glu Ser Val His Ile Leu Thr Asn Ala Cys Tyr
370                 375                 380

Asn Leu Leu Glu Lys Cys Ile Asn Gly Ile Thr Ala Asn Lys Glu Val
385                 390                 395                 400

Cys Glu Gly Tyr Val Tyr Asn Ser Ile Gly Ile Val Thr Tyr Leu Asn
                405                 410                 415

Pro Phe Ile Gly His His Asn Gly Asp Ile Val Gly Lys Ile Cys Ala
                420                 425                 430

Glu Thr Gly Lys Ser Val Arg Glu Val Val Leu Glu Arg Gly Leu Leu
    435                 440                 445

Thr Glu Ala Glu Leu Asp Asp Ile Phe Ser Val Gln Asn Leu Met His
450                 455                 460

Pro Ala Tyr Lys Ala Lys Arg Tyr Thr Asp Glu Ser Glu Gln
465                 470                 475

<210> SEQ ID NO 4
<211> LENGTH: 1437
<212> TYPE: DNA
<213> ORGANISM: Escherichia coli
<220> FEATURE:
<223> OTHER INFORMATION: L-aspartate lyase sequence

<400> SEQUENCE: 4
atgtcaaaca acattcgtat cgaagaagat ctgttgggta ccagggaagt tccagctgat      60
gcctactatg gtgttcacac tctgagagcg attgtaaact tctatatcag caacaacaaa     120
atcagtgata ttcctgaatt tgttcgcggt atggtaatgg ttaaaaaagc cgcagctatg     180
gcaaacaaag agctgcaaac cattcctaaa agtgtagcga atgccatcat gccgcatgt      240 gatgaagtcc tgaacaacgg aaaatgcatg atcagttcc ggtagacgt ctaccagggc      300 ggcgcaggta cttccgtaaa catgaacacc aacgaagtgc tggccaatat cggtctggaa     360
ctgatgggtc accaaaaagg tgaatatcag tacctgaacc cgaacgacca tgttaacaaa     420
tgtcagtcca ctaacgacgc ctacccgacc ggtttccgta tcgcagttta ctcttccctg     480
```

```
attaagctgg tagatgcgat taaccaactg cgtgaaggct ttgaacgtaa agctgtcgaa     540
ttccaggaca tcctgaaaat gggtcgtacc cagctgcagg acgcagtacc gatgaccctc     600
ggtcaggaat tccgcgcttt cagcatcctg ctgaaagaag aagtgaaaaa catccaacgt     660
accgctgaac tgctgctgga agttaacctt ggtgcaacag caatcggtac tggtctgaac     720
acgccgaaag agtactctcc gctggcagtg aaaaaactgg ctgaagttac tggcttccca     780
tgcgtaccgg ctgaagacct gatcgaagcg acctctgact gcggcgctta tgttatggtt     840
cacggcgcgc tgaaacgcct ggctgtgaag atgtccaaaa tctgtaacga cctgcgcttg     900
ctctcttcag gcccacgtgc cggcctgaac gagatcaacc tgccggaact gcaggcgggc     960
tcttccatca tgccagctaa agtaaacccg gttgttccgg aagtggttaa ccaggtatgc    1020
ttcaaagtca tcggtaacga caccactgtt accatggcag cagaagcagg tcagctgcag    1080
ttgaacgtta tggagccggt cattggccag gccatgttcg aatccgttca cattctgacc    1140
aacgcttgct acaacctgct ggaaaaatgc attaacggca tcactgctaa caaagaagtg    1200
tgcgaaggtt acgtttacaa ctctatcggt atcgttactt acctgaaccc gttcatcggt    1260
caccacaacg gtgacatcgt gggtaaaatc tgtgccgaaa ccggtaagag tgtacgtgaa    1320
gtcgttctgg aacgcggtct gttgactgaa gcggaacttg acgatatttt ctccgtacag    1380
aatctgatgc acccggctta caaagcaaaa cgctatactg atgaaagcga acagtaa      1437

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
tttggatccg atgagcaacc actaccgcat cg                                      32

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
tttaagcttt caataagcgc cggacagcag                                         30

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
tttcatatga gcaaccacta ccgcatcg                                           28

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
tttctcgagt caataagcgc cggacagcag                                         30
```

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
tttaagctta tgagcaacca ctaccgcatc g                           31

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
tttggatccg atgtcaaaca acattcgtat cgaag                       35

<210> SEQ ID NO 11
<211> LENGTH: 37
<212> TYPE: DNA
<213> ORGANISM: Artificial Sequence
<220> FEATURE:
<223> OTHER INFORMATION: primer

<400> SEQUENCE: 11
tttaagcttt tactgttcgc tttcatcagt atagcgt                     37

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
tttcatatgt caaacaacat tcgtatcgaa gaag                        34

<210> SEQ ID NO 13
<211> LENGTH: 37
<212> TYPE: DNA
<213> ORGANISM: Artificial Sequence
<220> FEATURE:
<223> OTHER INFORMATION: primer

<400> SEQUENCE: 13
tttctcgagt tactgttcgc tttcatcagt atagcgt                     37

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
tttaagctta tgtcaaacaa cattcgtatc gaag                        34

<210> SEQ ID NO 15
<211> LENGTH: 52
<212> TYPE: DNA
<213> ORGANISM: Artificial Sequence
<220> FEATURE:

<223> OTHER INFORMATION: primer

<400> SEQUENCE: 15
cgaaaatccc taaggagctt aagcatgggc agcagccatc accatcatca cc　　　　　52

<210> SEQ ID NO 16
<211> LENGTH: 71
<212> TYPE: DNA
<213> ORGANISM: Artificial Sequence
<220> FEATURE:
<223> OTHER INFORMATION: primer

<400> SEQUENCE: 16
gcttaagctc cttagggatt ttcgattaaa gttaaacaaa attatttcta cagggaatt　　60 gttatccgct c　　　　　　　　　　　　　　　　　　　　　　　　　　71

<210> SEQ ID NO 17
<211> LENGTH: 55
<212> TYPE: DNA
<213> ORGANISM: Artificial Sequence
<220> FEATURE:
<223> OTHER INFORMATION: primer

<400> SEQUENCE: 17
catcaccgtt agacgaggag gtatcctatg gcagcagcc atcaccatca tcacc　　　　55

<210> SEQ ID NO 18
<211> LENGTH: 74
<212> TYPE: DNA
<213> ORGANISM: Artificial Sequence
<220> FEATURE:
<223> OTHER INFORMATION: primer

<400> SEQUENCE: 18
aggatacctc ctcgtctaac ggtgatgatt aaagttaaac aaaattattt ctacagggga　60 attgttatcc gctc　　　　　　　　　　　　　　　　　　　　　　　　74

<210> SEQ ID NO 19
<211> LENGTH: 51
<212> TYPE: DNA
<213> ORGANISM: Artificial Sequence
<220> FEATURE:
<223> OTHER INFORMATION: primer

<400> SEQUENCE: 19 aatacccta c taaggaggta agcatgggca gcagccatca ccatcatcac c　　　　51

<210> SEQ ID NO 20
<211> LENGTH: 70
<212> TYPE: DNA
<213> ORGANISM: Artificial Sequence
<220> FEATURE:
<223> OTHER INFORMATION: primer

<400> SEQUENCE: 20
gcttacctcc ttagtagggt attattaaag ttaaacaaaa ttatttctac agggaattg　60 ttatccgctc　　　　　　　　　　　　　　　　　　　　　　　　　　70

<210> SEQ ID NO 21
<211> LENGTH: 58
<212> TYPE: DNA
<213> ORGANISM: Artificial Sequence
<220> FEATURE:
<223> OTHER INFORMATION: primer

```
<400> SEQUENCE: 21
gaactcgaac atagtcttaa ggaggttcaa atgggcagca gccatcacca tcatcacc        58

<210> SEQ ID NO 22
<211> LENGTH: 77
<212> TYPE: DNA
<213> ORGANISM: Artificial Sequence
<220> FEATURE:
<223> OTHER INFORMATION: primer

<400> SEQUENCE: 22
ttgaacctcc ttaagactat gttcgagttc attaaagtta aacaaaatta tttctacagg       60
ggaattgtta tccgctc                                                      77

<210> SEQ ID NO 23
<211> LENGTH: 27
<212> TYPE: DNA
<213> ORGANISM: Artificial Sequence
<220> FEATURE:
<223> OTHER INFORMATION: RBS Sequence

<400> SEQUENCE: 23
catcaccgtt agacgaggag gtatcct                                           27

<210> SEQ ID NO 24
<211> LENGTH: 23
<212> TYPE: DNA
<213> ORGANISM: Artificial Sequence
<220> FEATURE:
<223> OTHER INFORMATION: RBS Sequence

<400> SEQUENCE: 24
aataccctac taaggaggta agc                                               23

<210> SEQ ID NO 25
<211> LENGTH: 30
<212> TYPE: DNA
<213> ORGANISM: Artificial Sequence
<220> FEATURE:
<223> OTHER INFORMATION: RBS Sequence

<400> SEQUENCE: 25
gaactcgaac atagtcttaa ggaggttcaa                                        30
```

METHOD FOR PREPARING L-ASPARTIC ACID WITH MALEIC ACID BY WHOLE-CELL BIOCATALYSIS

This application is the National Stage Application of PCT/CN2018/074337, filed on Jan. 26, 2018, which claims priority to Chinese Patent Application No. 201711374147.7, filed on Dec. 19, 2017, which is incorporated by reference for all purposes as if fully set forth herein.

FIELD OF THE INVENTION

The present invention relates to the technical field of bioengineering, and more particularly to a method for synthesizing L-aspartic acid with maleic acid by whole-cell biocatalysis.

DESCRIPTION OF THE RELATED ART

L-aspartic acid is one of the 20 essential amino acids that make up proteins. It has been extensively used in the fields of food, medicine, chemical and others, thus having great potential of development in the market.

Currently the process for industrial production of L-aspartic acid mainly comprises converting the maleic anhydride as raw material into fumarate in the presence of an inorganic catalyst at a strongly acidic pH (about pH 1); separating and purifying the fumarate, then reacting fumarate with excess ammonia in the presence of L-aspartate lyase to produce ammonium L-asparate, neutralizing the excess ammonia in the reaction solution, and separating and purifying to obtain the product L-aspartic acid. Although the process is simple, the disadvantages are obvious. The reaction needs to be carried out at a high temperature, under a high pressure, and in the presence of a transition metal catalyst and a strong acid. The requirements on the equipment are strict, serious environmental pollution is caused, and the intermediate product fumarate needs to be separated and purified, and thus reduced yield is caused. In contrast, the whole-cell catalytic conversion method by means of double enzyme-coupling has the advantages of high specificity, high conversion rate, simple process, low equipment investment and low environmental pollution, and thus has a good application prospect.

At present, there are few studies on the synthesis of L-aspartic acid with maleate by whole-cell biocatalysis. Most of them are focused on the study of fumarate as a substrate, mainly due to the limitations from maleate cis-trans isomerase, such as poor stability, low enzyme activity, and difficulty in heterologous expression.

SUMMARY OF THE INVENTION

To solve the above technical problems, an object of the present invention is to provide a method for preparing L-aspartic acid with maleic acid by whole-cell biocatalysis. A recombinant strain co-expressing maleate cis-trans isomerase (derived from *Serratia marcescens*) and L-aspartate lyase (derived from *E. coli*) is provided, and engineered and optimized to produce L-aspartic acid from maleic acid with a high conversion rate by whole-cell catalyzing.

For the above purpose, the following technical solutions are adopted in the invention.

In one aspect, the present invention provides a method for preparing L-aspartic acid, the method comprises catalyzing a substrate maleic acid by using a recombinant strain co-expressing maleate cis-trans isomerase and L-aspartate lyase or an enzyme produced from the recombinant strain as a catalyst, to produce L-aspartic acid.

In an embodiment of the invention, the recombinant strain co-expressing maleate cis-trans isomerase and L-aspartate lyase is produced by expressing, in *E. coli* as a host, the recombinant expression vector pRSFDuet-1-maiA-aspA constructed with pRSFDuet-1 that is an expression vector.

In an embodiment of the present invention, the maleate cis-trans isomerase is derived from *Serratia marcescens*, and the L-aspartate lyase is derived from *E. coli*.

In an embodiment of the present invention, the *E. coli* is *E. coli* BL21 (DE3) ΔfumAC with fumA-fumC gene knockout from the genome.

In an embodiment of the present invention, the gene encoding the maleate cis-trans isomerase has a nucleotide sequence as shown in SEQ ID NO:2.

In an embodiment of the present invention, the gene encoding the L-aspartate lyase has a nucleotide sequence as shown in SEQ ID NO:4.

In an embodiment of the present invention, the glycine at position 27 in the sequence of SEQ ID NO:2 encoding the maleate cis-trans isomerase is mutated into alanine and the glycine at position 171 is mutated into alanine; or the glycine at position 27 in the sequence of SEQ ID NO:2 is mutated into alanine and the lysine at position 104 is mutated into arginine.

In an embodiment of the present invention, on the basis of the sequence as shown in SEQ ID NO:4, the RBS sequence in the gene encoding the L-aspartate lyase is replaced by the sequence as shown in SEQ ID NO:23, SEQ ID NO:24, or SEQ ID NO:25.

In an embodiment of the present invention, a 2 M maleic acid solution of pH 8.0 is used as a substrate, and a resting cell suspension having a cell concentration with $OD_{600}$ of 40 is added for catalyzing, in which the volume ratio of the resting cell suspension to the substrate (maleic acid) solution is 2:8.

The method is performed in a 50 mM $Na_2HPO_4$—$KH_2PO_4$ buffer of pH 8.0, and the reaction temperature is 37° C.

In another aspect, the present invention further provides a recombinant strain co-expressing maleate cis-trans isomerase and L-aspartate lyase efficiently. The recombinant strain is produced by expressing, in *E. coli* as a host, a recombinant expression vector pRSFDuet-1-maiA-aspA constructed with pRSFDuet-1 that is an expression vector.

In an embodiment of the present invention, the *E. coli* is *E. coli* BL21 (DE3) ΔfumAC with fumA-fumC gene knockout from the genome.

In an embodiment of the present invention, the gene encoding the maleate cis-trans isomerase has a nucleotide sequence as shown in SEQ ID NO:2.

In an embodiment of the present invention, the gene encoding the L-aspartate lyase has a nucleotide sequence as shown in SEQ ID NO:4.

In an embodiment of the present invention, the glycine at position 27 in the sequence of SEQ ID NO:2 encoding the maleate cis-trans isomerase is mutated into alanine and the glycine at position 171 is mutated into alanine; or the glycine at position 27 in the sequence of SEQ ID NO:2 is mutated into alanine and the lysine at position 104 is mutated into arginine.

In an embodiment of the present invention, on the basis of the sequence as shown in SEQ ID NO:4, the RBS sequence in the gene encoding the L-aspartate lyase is replaced by the sequence as shown in SEQ ID NO:23, SEQ ID NO:24, or SEQ ID NO:25.

By means of the above technical solutions, as compared with the prior art, the invention has the following advantages: in the method of the present invention, relatively inexpensive maleic acid is utilized to produce L-aspartic acid, where maleic acid is reacted completely in 40-120 min, there is almost no buildup of the intermediate fumarate, and the conversion rate is up to 98% or more.

DETAILED DESCRIPTION OF THE PREFERRED EMBODIMENTS

Figure 1:
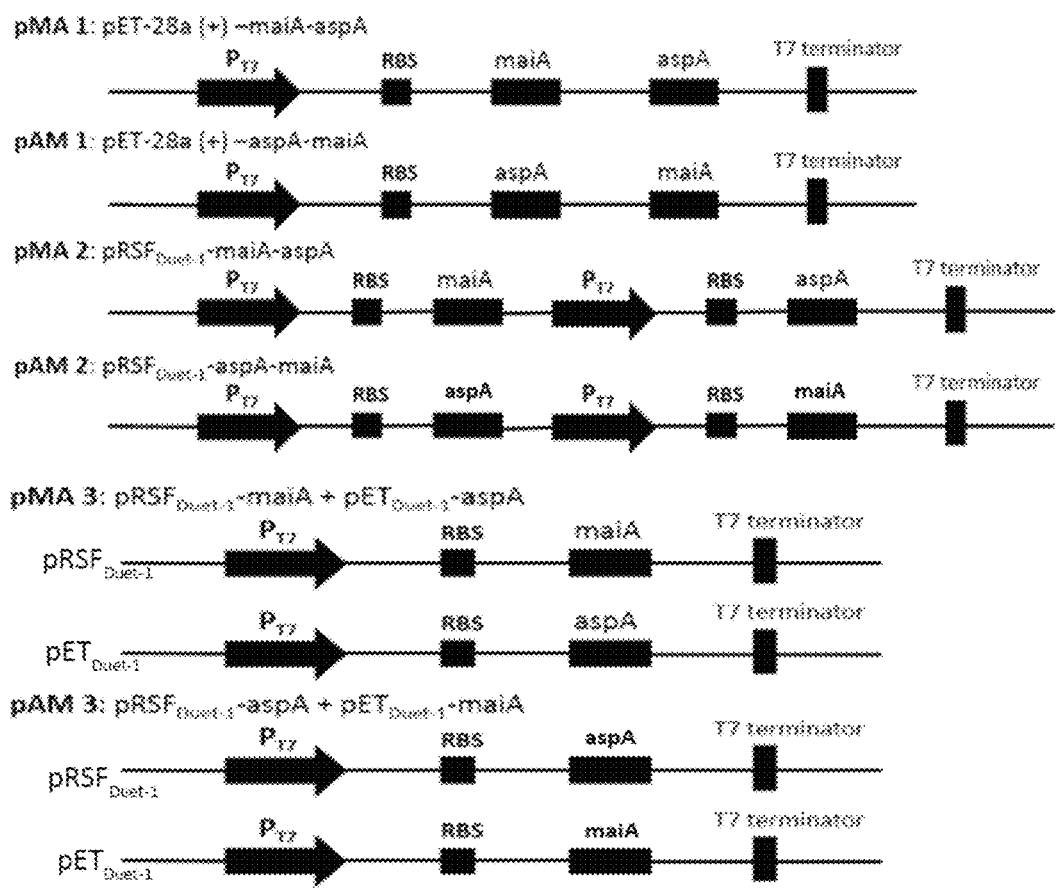
FIG. 1 shows various strategies for the co-expression of MaiA and AspA according to the invention.

The invention will be further illustrated in more detail with reference to the accompanying drawings and embodiments. It is noted that, the following embodiments only are intended for purposes of illustration, but are not intended to limit the scope of the present invention.

Detection Methods for Maleic Acid, Fumaric Acid, and L-Aspartic Acid:

The concentrations of maleic acid, fumaric acid, and L-aspartic acid are all detected by high-performance liquid chromatography (HPLC). The detection conditions for maleic acid and fumaric acid by HPLC include: chromatographic column: Prevail Organic Acid (250 mm×4.6 mm, 5 m; Grace Davison Discovery Sciences); mobile phase: pH 2.5, 25 mM $K_2HPO_4$ solution, flow rate 1 mL/min; column temperature: 40° C.; wavelength of UV detector: 210 nm; and injection volume: 10 μL. The detection of L-aspartic acid comprises derivatization with phenyl isothiocyanate (PITC) to attach a phenyl ring to the amino terminus for convenient separation. The method of derivatization comprises adding 250 μL of 1 M triethyl amine-acetonitrile solution and 250 μL of 0.1 M PITC-acetonitrile solution to 500 μL of the reaction solution, mixing uniformly by shaking, and reacting for 1 h in the dark. After derivatization, the residual derivatization reagent is extracted out with 700 μL of n-hexane by shaking for 30 s, and the reaction solution is allowed to stand. After the reaction solution was obviously layered, the lower solution was pipetted and filtered with a 0.22 μm needle-type organic filter. Detection conditions by HPLC: chromatographic column: La Chrom C18 (5 m, 4.6 mm×250 mm), and gradient elution with a mobile phase A of 80% acetonitrile solution and a mobile phase B of 0.1 M sodium acetate-acetonitrile solution (97:3); gradient elution conditions: gradient from 95% to 65% of mobile phase B over 0-35 min; gradient from 65% to 95% of mobile phase B over 35-40 min; 95% of mobile phase B over 40-45 min; detection temperature 40° C., and detection wavelength 254 nm.

Embodiment 1

Construction of a Recombinant Strain Co-Expressing Maleate Cis-Trans Isomerase and L-Aspartate Lyase 1) The maleate cis-trans isomerase has an amino acid sequence as shown in SEQ ID NO:1, and the gene encoding the maleate cis-trans isomerase has a nucleotide sequence as shown in SEQ ID NO:2. The L-aspartate lyase has an amino acid sequence as shown in SEQ ID NO:3, and the gene encoding the L-aspartate lyase has a nucleotide sequence as shown in SEQ ID NO:4. According to the target gene and the vector, the cleavage sites were selected and the primers were designed (see Table 1).

TABLE 1

Design of adapter primer for cleavage

| Gene | Primer | Primer sequence (5'--- 3') | Cleavage site |
|---|---|---|---|
| maiA | P1 | TTT<u>GGATCC</u>GATGAGCAACCACTACCGC ATCG | BamHI |
|  | P2 | TTT<u>AAGCTT</u>TCAATAAGCGCCGGACAGCAG | HindIII |
|  | P3 | TTT<u>CATATG</u>AGCAACCACTACCGCATCG | NdeI |
|  | P4 | TTT<u>CTCGAG</u>TCAATAAGCGCCGGACAGCAG | XhoI |
|  | P5 | TTT<u>AAGCTT</u>ATGAGCAACCACTACCGCATCG | HindIII |
| aspA | P6 | TTT<u>GGATCC</u>GATGTCAAACAACATTCGTA TCGAAG | BamHI |
|  | P7 | TTT<u>AAGCTT</u>TTACTGTTCGCTTTCATCAG TATAGCGT | HindIII |

TABLE 1-continued

Design of adapter primer for cleavage

| Gene Primer | Primer sequence (5'--- 3') | Cleavage site |
|---|---|---|
| P8 | TTT<u>CATATG</u>TCAAACAACATTCGTATCGA AGAAG | NdeI |
| P9 | TTT<u>CTCGAG</u>TTACTGTTCGCTTTCATCAG TATAGCGT | XhoI |
| P10 | TTT<u>AAGCTT</u>ATGTCAAACAACATTCGTAT CGAAG | HindIII |

Note:
The underlined sequences are the cleavage sites

Figure 2:
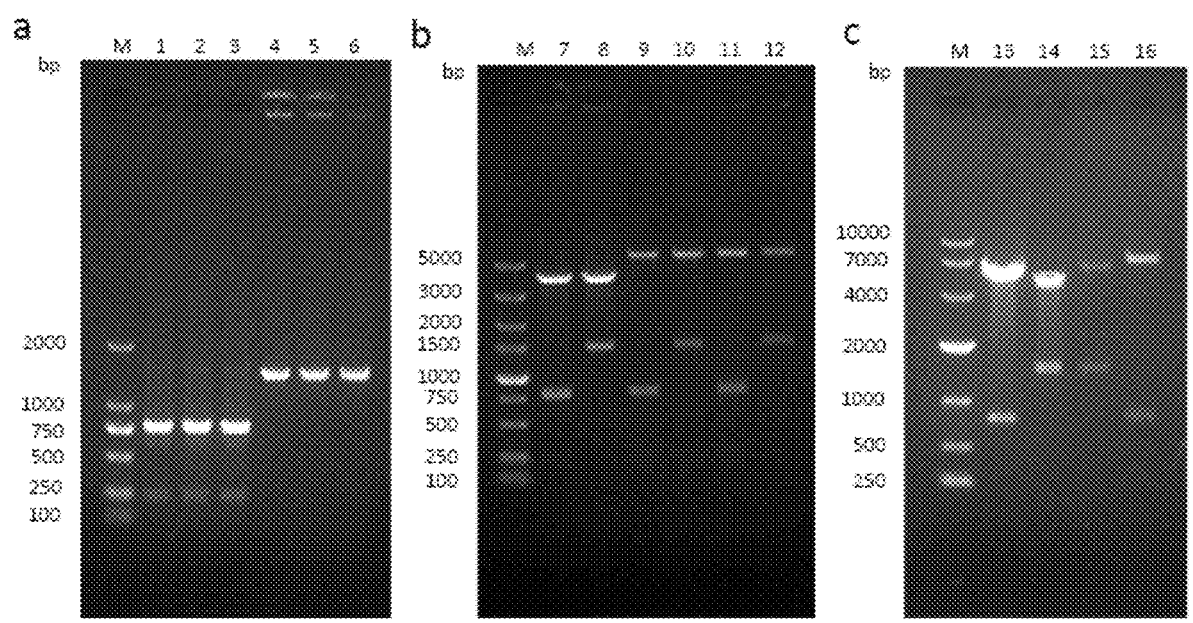
FIG. 2 shows the PCR amplification of the maiA and aspA gene and the verification by restriction endonuclease cleavage of the recombinant plasmids, in which M: marker; 1. PCR product of BamHI-maiA-Hind III; 2: PCR product of NdeI-maiA-XhoI; 3: PCR product of HindIII-maiA-XhoI; 4: PCR product of BamHI-aspA-HindIII; 5: PCR product of NdeI-aspA-XhoI; 6: PCR product of HindIII-aspA-XhoI; 7: verification by double restriction endonuclease cleavage of pRSF$_{Duet-1}$-maiA recombinant plasmid; 8: verification by double restriction endonuclease cleavage of pRSF$_{Duet-1}$-aspA recombinant plasmid; 9: verification by double restriction endonuclease cleavage of pET$_{Duet-1}$-maiA recombinant plasmid; 10: verification by double restriction endonuclease cleavage of pET$_{Duet-1}$-aspA recombinant plasmid; 11: verification by double restriction endonuclease cleavage of pET-28a(+)-maiA recombinant plasmid; 12: verification by double restriction endonuclease cleavage of pET-28a(+)-aspA recombinant plasmid; 13: verification by double restriction endonuclease cleavage of pRSF$_{Duet-1}$-aspA-maiA recombinant plasmid; 14: verification by double restriction endonuclease cleavage of pRSF$_{Duet-1}$-maiA-aspA recombinant plasmid; 15: verification by double restriction endonuclease cleavage of pET-28a(+)-maiA-aspA recombinant plasmid; and 16: verification by double restriction endonuclease cleavage of pET-28a(+)-aspA-maiA recombinant plasmid.

2) PCR was carried out using pET-24a (+)-maiA and pET-28a (+)-aspA as templates, respectively, to obtain maiA and aspA gene fragments with different cleavage sites as shown in FIG. 2a: BamHI-maiA-HindIII, NdeI-maiA-XhoI, HindIII-maiA-XhoI, BamHI-aspA-HindIII, NdeI-aspA-XhoI, HindIII-aspA-XhoI;

3) The PCR fragments were purified and cleaved with two corresponding enzymes for 2 h. The corresponding plasmid vectors pRSF$_{Duet-1}$, pET$_{Duet-1}$, and pET-28a(+) were cleaved with two corresponding enzymes for 2 h, and then the cleaved products were recovered by gel extraction, and purified.

4) The concentrations of the recovered gene and vector fragments were determined by a nucleic acid quantification instrument. The gene and vector fragments were mixed at a ratio of gene fragment: vector fragment=3:1, and then T$_4$ DNA ligase was added for ligation at 16° C. overnight.

5) The ligation product was transformed into competent JM109 cells, and then plated onto a corresponding antibiotic-resistant LB plate of the vector.

6) Verification by colony PCR was performed first, then a single colony was picked up to 5 mL of LB liquid test medium (10 g peptone, 5 g yeast extract, and 10 g NaCl, to make 1 L) with antibiotic concentration of 50 µg/mL, and cultured at 37° C. and 200 rpm for 8 h. The plasmid was extracted, cleaved by two enzymes, and verified (FIGS. 2b and 2c). The clone verified to be correct was sequenced.

7) The recombinant plasmid sequenced to be correct was transformed into the competent host cells E. coli BL21 (DE3) ΔfumAC (where the E. coli BL21 (DE3) ΔfumAC is produced as described in Fang Yueqin, Zhou Li, Zhou Zhemin. Efficient Production of Fumarate from Maleate Using Recombinant E. coli as Whole Cell Biocatalyst [J]. Journal of Food Science and Biotechnology, 2016, 35(12): 1323-1329.), and then coated onto a corresponding antibiotic-resistant LB plate of the vector. Single colonies were picked up to obtain six co-expression systems: pMA 1: pET-28a (+)-maiA-aspA; pAM 1: pET-28a (+)-aspA-maiA; pMA 2: pRSFDuet-1-maiA-aspA; pAM 2: pRSFDuet-1-aspA-maiA; pMA 3: pRSFDuet-1-maiA-pETDuet-1-aspA; and pAM 3: pRSFDuet-1-aspA-pETDuet-1-maiA 6.

8) A single colony was picked up, inoculated into 5 mL of LB medium with antibiotic concentration of 50 g/mL, incubated at 37° C. and 200 rpm for 8 h, and then transferred to a 250 mL shake flask containing 50 mL of 2 YT medium (16 g peptone, 10 g yeast extract, and 5 g NaCl, to make 1 L) with an antibiotic concentration of 50 g/mL by inoculating in an amount of 2%, and incubated at 37° C. and 200 rpm until the OD was 0.8. Then IPTG was added at a final concentration of 0.2 mmol/L to induce the expression at 20° C. for 20 h.

Figure 3:
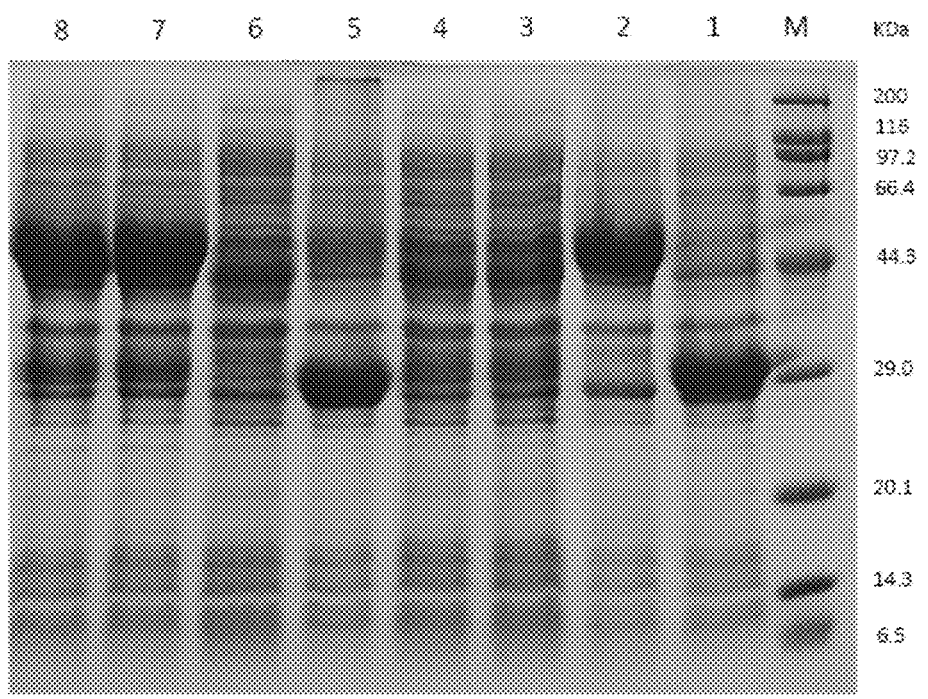
FIG. 3 shows the results of SDS-PAGE of various co-expressed genes, in which M: marker; 1: the expression result of pRSF$_{Duet-1}$-maiA; 2: the expression result of pRSF$_{Duet-1}$-aspA; 3: the expression result of pMA 1; 4: the expression result of pAM 1; 5: the expression result of pMA 2; 6: the expression result of pAM 2; 7: the expression result of pMA 3; and 8: the expression result of pAM 3.

9) The same amount of cells induced to express were taken, collected by centrifugation, resuspended in 50 mM Na$_2$HPO$_4$—KH$_2$PO$_4$ buffer of pH 8.0, and ultrasonically homogenized to obtain a crude enzyme solution. The expression of the target proteins was analyzed by SDS-PAGE analysis (as shown in FIG. 3). When MaiA and AspA are expressed separately, the expression levels are both high. When they are expressed in tandem, their expression levels are correspondingly reduced. The expression levels of the two enzymes differ greatly for different tandem patterns. The expression levels of the two enzymes in the tandem systems pMA 1 and pAM 1 are lower; the expression of MaiA in the tandem system pMA 2 is higher, and the expression of AspA is lower; the two enzymes have almost no expression in the tandem system pAM 2; and the expression of AspA in the tandem systems pMA3 and pAM3 is higher, and the expression of MaiA is lower. 100 µL of the crude enzyme solution produced from each recombinant cell was added to 50 L of 2 M ammonium maleate solution of pH 8.0. The system was made up to 500 L with 500 mM Na$_2$HPO$_4$—KH$_2$PO$_4$ buffer (pH 8.0), reacted at 40° C. for 10 min, and then boiled at 100° C. for 10 min. After centrifugation, the supernatant was collected, and the contents of maleic acid, fumaric acid, and L-aspartic acid in the supernatant were detected. As shown in Table 2, the tandem system pMA 2 has the best catalytic effect for the production of L-aspartic acid. Because the enzyme activity of AspA is much higher than that of MaiA, the rate limiting factor of the catalytic system is the total enzyme activity of MaiA. As such, when the expression level of MaiA is higher, the catalysis effect is better.

TABLE 2

Comparison of the catalytic effects for 200 mM maleate of crude enzymes from recombinant strains

| Recombinant strain | Substrate (maleate) mM | Intermediate product (fumarate) mM | End product (L-aspartic acid) mM |
|---|---|---|---|
| pMA 1 | 156.3 | 0.8 | 49.1 |
| pAM 1 | 170.7 | 0.5 | 30.8 |
| pMA 2 | 41.4 | 0.2 | 161.2 |
| pAM 2 | 200 | 0 | 0 |
| pMA 3 | 134.8 | 0.1 | 65.1 |
| pAM 3 | 138.4 | 0.1 | 63.6 |

Embodiment 2

Figure 4:
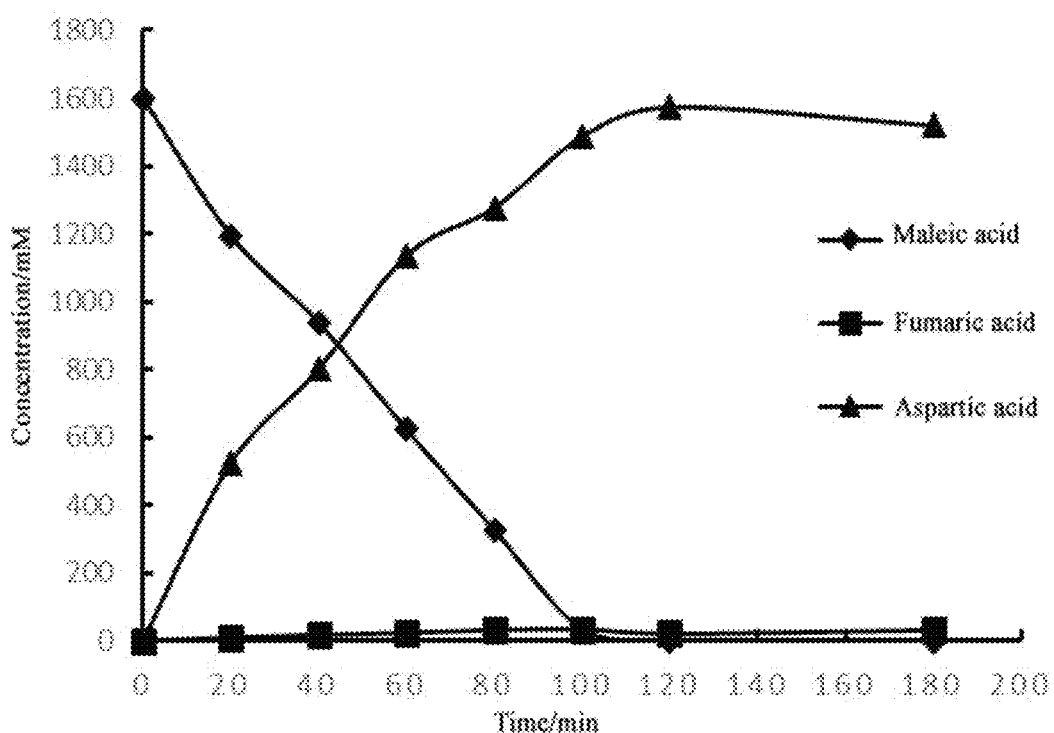
FIG. 4 shows the results of whole-cell biocatalysis by pMA 2.

Production of L-Aspartic Acid from Maleic Acid by Whole-Cell Biocatalysis by the Recombinant Strain pMA 2 Co-Expressing Maleate Cis-Trans Isomerase and L-Aspartate Lyase A maleic acid solution (pH 8.0) was formulated, and wherein the pH of the maleic acid solution was adjusted to 8.0 with aqueous ammonia. The pMA 2 cells induced to express in embodiment 1 were collected, re-suspended in 50 mM Na$_2$HPO$_4$—KH$_2$PO$_4$ buffer (pH 8.0), and diluted to an OD$_{600}$ of 40. Then, 20% (by volume) of the resting cells was mixed with 80% (by volume) of the substrate maleic acid to give a reaction system of 30 mL. The reaction was catalyzed in a shaker at 200 r/min and 37° C., and samples were taken every 20 minutes to determine the contents of maleic acid, fumaric acid and L-aspartic acid in the reaction solution. As shown in FIG. 4, the substrate maleic acid is completely reacted in 120 min, there is almost no buildup of the intermediate fumaric acid, and the conversion rate reaches 98% or more.

Embodiment 3

Engineering of RBS in the MaiA Gene Sequence (1) RBS sequences with different rates of translation initiation were predicted by the RBS Calculator software. Four RBS sequences with different rates of translation initiation were selected, and primers were designed (Table 3).

TABLE 3

Primer design for engineering of RBS in MaiA

| Initiation rate of RBS translation | Primer | Primer sequence (5'--- 3') |
|---|---|---|
| 90504.51 | maiA-1up | *CGAAAATCCCTAAGGAGCTTAAGC*ATGGGCAGCAGCCATCACCAT CATCACC (SEQ ID NO: 15) |
|  | maiA-1down | *GCTTAAGCTCCTTAGGGATTTTCG*ATTAAAGTTAAACAAAATTAT TTCTACAGGGGAATTGTTATCCGCTC (SEQ ID NO: 16) |
| 212828.18 | maiA-2up | *CATCACCGTTAGACGAGGAGGTATCCT*ATGGGCAGCAGCCATCAC CATCATCACC (SEQ ID NO: 17) |
|  | maiA-2down | *AGGATACCTCCTCGTCTAACGGTGATG*ATTAAAGTTAAACAAAAT TATTTCTACAGGGGAATTGTTATCCGCTC (SEQ ID NO: 18) |
| 318342.84 | maiA-3up | *AATACCCTACTAAGGAGGTAAGC*ATGGGCAGCAGCCATCACCATC ATCACC (SEQ ID NO: 19) |
|  | maiA-3down | *GCTTACCTCCTTAGTAGGGTATT*ATTAAAGTTAAACAAAATTATT TCTACAGGGGAATTGTTATCCGCTC (SEQ ID NO: 20) |
| 370978.54 | maiA-4up | *GAACTCGAACATAGTCTTAAGGAGGTTCAA*ATGGGCAGCAGCCAT CACCATCATCACC (SEQ ID NO: 21) |
|  | maiA-4down | *TTGAACCTCCTTAAGACTATGTTCGAGTTC*ATTAAAGTTAAACAAA ATTATTTCTACAGGGGAATTGTTATCCGCTC (SEQ ID NO: 22) |

Note:
The RBS sequences predicted by the RBS Calculator are underlined in italics.

(2) Using pMA 2 as a template, the original RBS sequence of MaiA in pRSFDuet-1-maiA-aspA was replaced by whole plasmid PCR, and the PCR product was digested overnight with DpnI.

(3) The digested product was transformed into competent JM109 cells and then plated onto an LB plate with kanamycin.

(4) Single colonies were picked for sequencing, and the correctly mutated recombinant plasmid mutants were transformed into the expression host competent E. coli BL21 (DE3) ΔfumAC cells, and then plated onto an LB plate with kanamycin to obtain four strains expressing MaiA having RBS with different rates of translation initiation, that is, pMA 2-1, pMA 2-2, pMA 2-3, and pMA 2-4.

(5) Single colonies were picked and inoculated respectively into 5 mL of LB medium with antibiotic concentration of 50 g/mL, cultured at 37° C. and 200 rpm for 8 h, and then transferred to a 250 mL shake flask containing 50 mL of 2 YT medium (16 g peptone, 10 g yeast extract, and 5 g NaCl, to make 1 L) with an antibiotic concentration of 50 g/mL by inoculating in an amount of 2%, and incubated at 37° C. and 200 rpm until the $OD_{600}$ was 0.8. Then IPTG was added at a final concentration of 0.2 mmol/L to induce the expression at 20° C. for 20 h.

Figure 5:
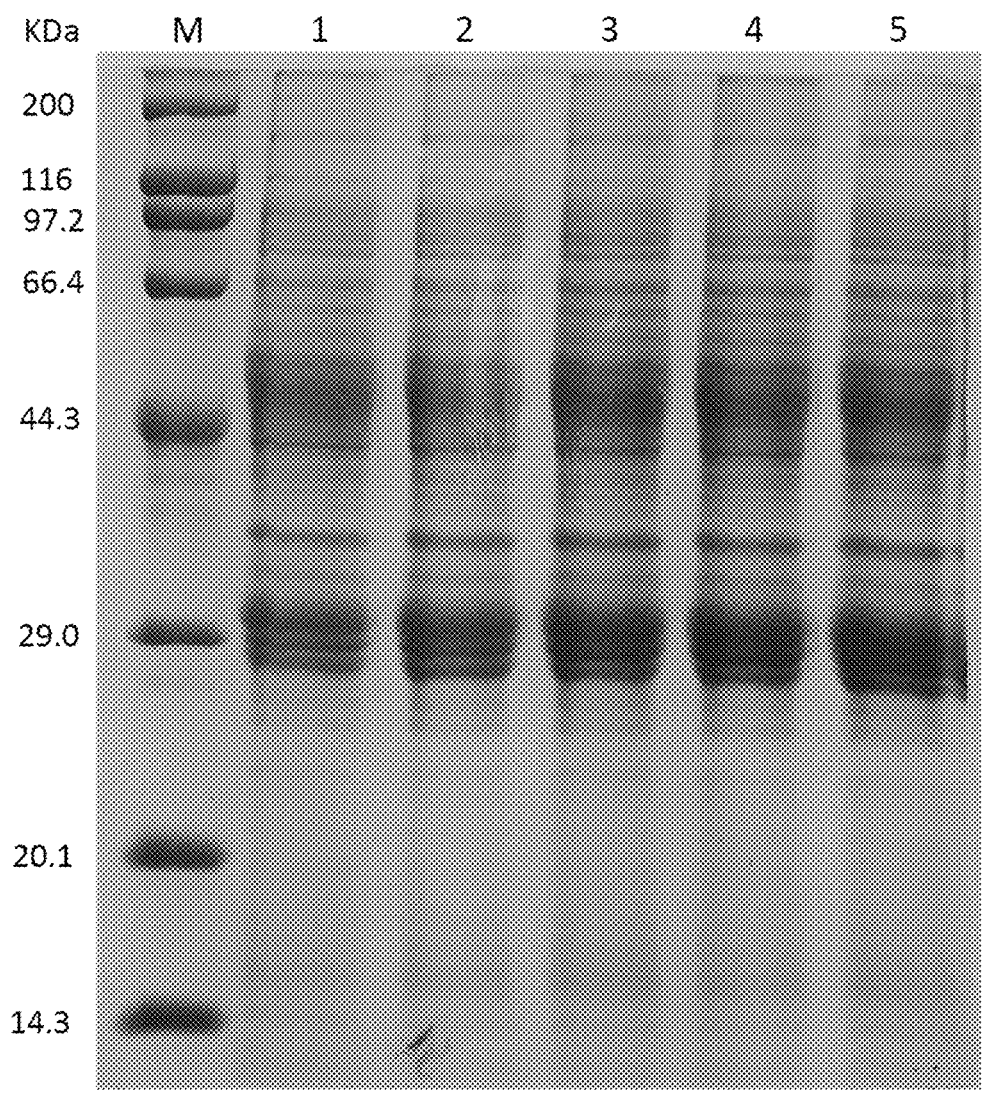
FIG. 5 shows the results of SDS-PAGE after the RBS of MaiA in pMA 2 is engineered, in which M: marker; 1: the expression result of pMA 2; 2: the expression result of pMA 2-1; 3: the expression result of pMA 2-2; 4: the expression result of pMA 2-3; and 5: the expression result of pMA 2-4.

(6) The same amount of cells were collected by centrifugation, resuspended in 50 mM $Na_2HPO_4$—$KH_2PO_4$ buffer pH 8.0, and ultrasonically homogenized to obtain a crude enzyme solution. The expression level of MaiA was analyzed by SDS-PAGE analysis (as shown in FIG. 5). As the rate of translation initiation of RBS increases, the expression level of MaiA rises. In the case of pMA 2-4, the expression level is the maximum. Next, whole-cell catalysis by pMA 2-4 was performed.

Figure 6:
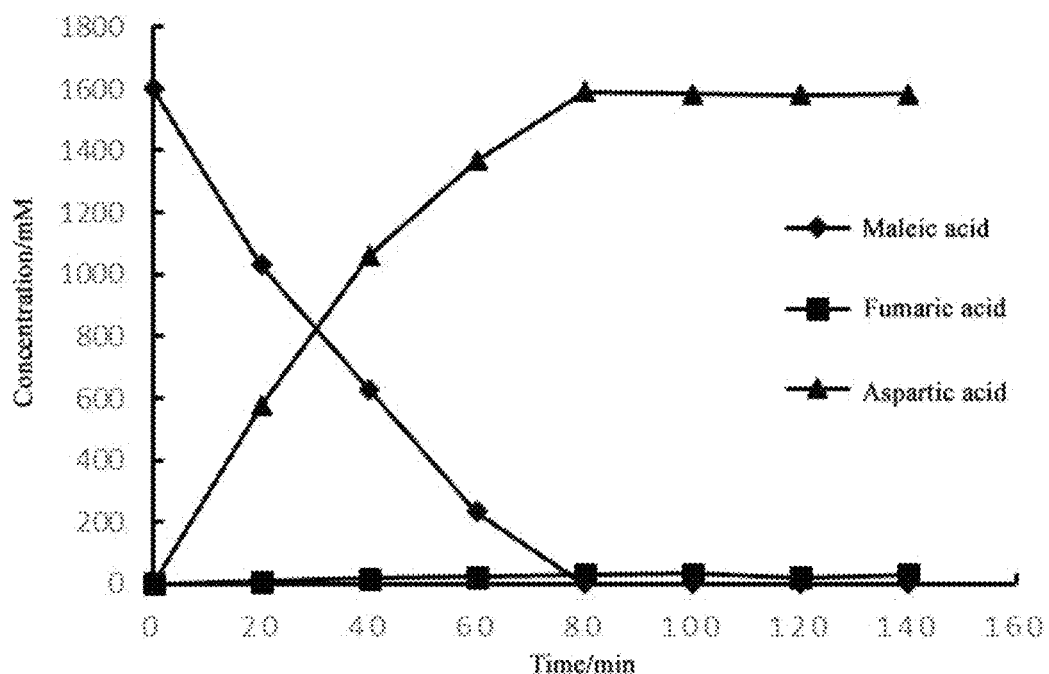
FIG. 6 shows the results of whole-cell biocatalysis by pMA 2-4.

(7) A maleic acid solution (pH 8.0) was formulated, and wherein the pH of the maleic acid solution was adjusted to 8.0 with aqueous ammonia. The pMA 2-4 cells induced to express in Step (5) were collected, re-suspended in 50 mM $Na_2HPO_4$—$KH_2PO_4$ buffer (pH 8.0), and diluted until $OD_{600}$ was 40. Then, 20% (by volume) of the resting cells was mixed with 80% (by volume) of the substrate maleic acid to give a reaction system of 30 mL. The reaction was catalyzed in a shaker at 200 r/min and 37° C., and samples were taken every 20 minutes to determine the contents of maleic acid, fumaric acid and L-aspartic acid in the reaction solution. As shown in FIG. 6, under the same conditions, the substrate maleic acid is completely catalytically converted by pMA 2-4 in only 80 min, there is almost no buildup of the intermediate fumaric acid, and the conversion rate reaches 98% or more.

Embodiment 4

Mutation of Maleate Cis-Trans Isomerase (1) The mutant maiA gene fragments maiA(G27A-G171A) and maiA(G27A-K104R) were obtained by PCR using pET-24a (+)-maiA(G27A-G171A) and pET-24a (+)-maiA(G27A-K104R) as templates.

(2) As described in Steps 2-9 of embodiment 1, the recombinant strain was constructed, induced and cultured. The whole-cell reaction was carried out as described in embodiment 2.

Figure 7:
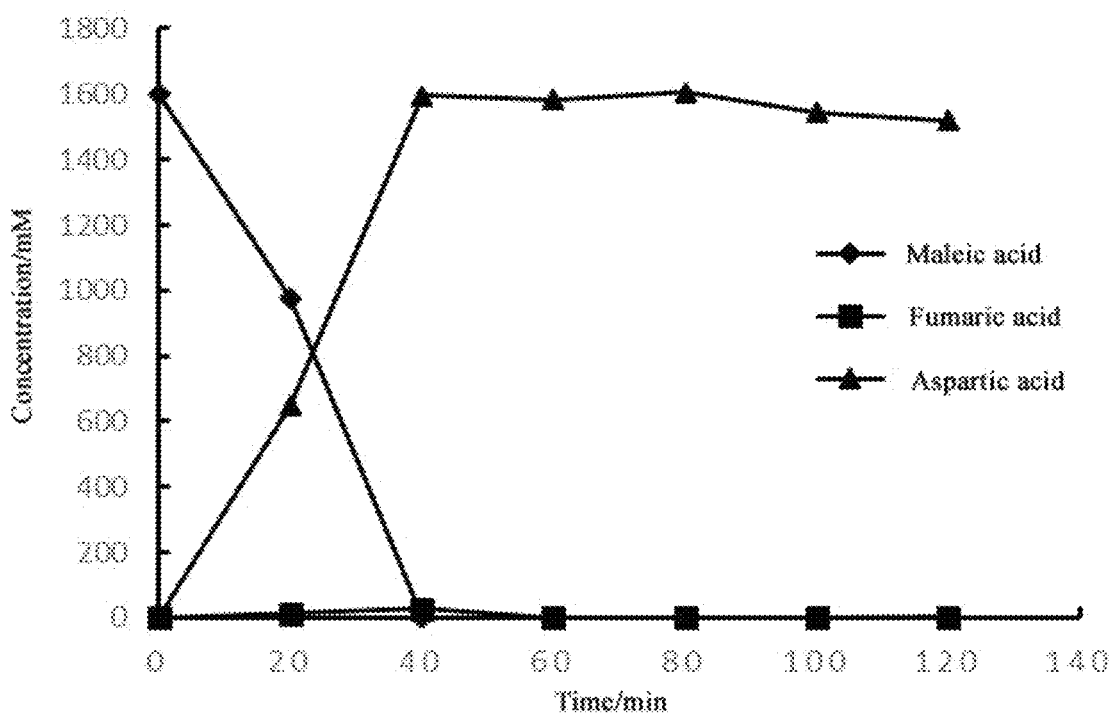
FIG. 7 shows the results of whole-cell biocatalysis by pMA 2-4 (G27A-G171A)
Figure 8:
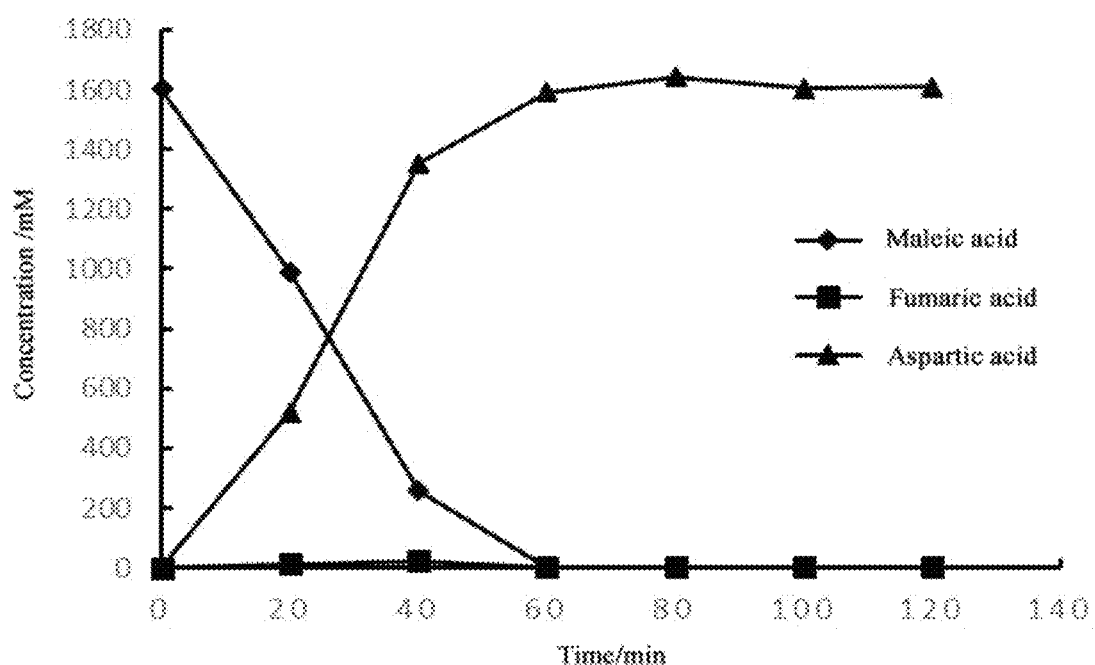
FIG. 8 shows the results of whole-cell biocatalysis by pMA 2-4 (G27A-K104R).

The half-life of G27A-G171A at 55° C. is 2.9 times that of wild type, and the enzyme activity is 1.96 times that of wild type. The half-life of G27A-K104R at 55° C. is 4.18 times that of wild type, and the enzyme activity is 1.59 times that of wild type. The results are shown in FIG. 7. Compared with embodiment 3, the substrate maleic acid is completely catalytically converted by pMA 2-4(G27A-G171A) in only 40 min, there is almost no buildup of the intermediate fumaric acid, and the conversion rate reaches 98% or more. As shown in FIG. 8, under the same conditions, the substrate maleic acid is completely catalytically converted by pMA 2-4 (G27A-K104R) in only 60 min, there is almost no buildup of the intermediate fumaric acid, and the conversion rate reaches 98% or more.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. A recombinant strain co-expressing maleate cis-trans isomerase and L-aspartate lyase, wherein the recombinant strain is produced by expressing, in *Escherichia coli* as a host, a recombinant expression vector pRSFDuet-1-maiA-aspA constructed with pRSFDuet-1 which is used as an expression vector.

2. The recombinant strain as claimed in claim 1, wherein the *Escherichia coli* is *Escherichia coli* BL21 (DE3) ΔfumAC with fumA-fumC gene knockout from the genome.

3. The recombinant strain co-expressing maleate cis-trans isomerase and L-aspartate lyase as claimed in claim 1, wherein the gene encoding the maleate cis-trans isomerase has:
   a nucleotide sequence as shown in SEQ ID NO:2; or
   a nucleotide sequence as shown in SEQ ID NO:2 in which the glycine at position 27 is mutated into alanine and the glycine at position 171 is mutated into alanine; or
   a nucleotide sequence as shown in SEQ ID NO:2 in which the glycine at position 27 is mutated into alanine and the lysine at position 104 is mutated into arginine.

4. The recombinant strain co-expressing maleate cis-trans isomerase and L-aspartate lyase as claimed in claim 1, wherein the gene encoding the L-aspartate lyase has a nucleotide sequence as shown in SEQ ID NO:4.

5. The recombinant strain co-expressing maleate cis-trans isomerase and L-aspartate lyase as claimed in claim 4, wherein the Ribosome Binding Site (RBS) sequence in the gene encoding the L-aspartate lyase is replaced by the sequence as shown in SEQ ID NO:23, SEQ ID NO:24, or SEQ ID NO:25.

6. A method for preparing L-aspartic acid, comprising: culturing a recombinant strain co-expressing maleate cis-trans isomerase and L-aspartate lyase in a culture medium comprising maleic acid, wherein the recombinant strain is able to catalyze the substrate maleic acid in the culture medium to produce the L-aspartic acid, wherein the recombinant strain co-expressing maleate cis-trans isomerase and L-aspartate lyase is *Escherichia coli* which has been transformed with recombinant expression vector pRSFDuet-1-maiA-aspA constructed with pRSFDuet-1 that is an expression vector.

7. The method for preparing L-aspartic acid as claimed in claim 6, wherein the maleate cis-trans isomerase is derived from *Serratia marcescens*, and the L-aspartate lyase is derived from *Escherichia coli*.

8. The method for preparing L-aspartic acid as claimed in claim 7, wherein the *Escherichia coli* is *Escherichia coli* BL21 (DE3) ΔfumAC with fumA-fumC gene knockout from the genome.

9. The method for preparing L-aspartic acid as claimed in claim 6, wherein the gene encoding the maleate cis-trans isomerase has:

a nucleotide sequence as shown in SEQ ID NO:2; or a nucleotide sequence as shown in SEQ ID NO:2 in which the glycine at position 27 is mutated into alanine and the glycine at position 171 is mutated into alanine; or a nucleotide sequence as shown in SEQ ID NO:2 in which the glycine at position 27 is mutated into alanine and the lysine at position 104 is mutated into arginine.

10. The method for preparing L-aspartic acid as claimed in claim 6, wherein the gene encoding the L-aspartate lyase has a nucleotide sequence as shown in SEQ ID NO:4.

11. The method for preparing L-aspartic acid as claimed in claim 10, wherein the Ribosome Binding Site (RBS) sequence in the gene encoding the L-aspartate lyase is replaced by the sequence as shown in SEQ ID NO:23, SEQ ID NO:24, or SEQ ID NO:25.

12. The method for preparing L-aspartic acid as claimed in claim 6, wherein a 2 M maleic acid solution of pH 8.0 is used as a substrate, and a resting cell suspension of the recombinant strain having a cell concentration with $OD_{600}$ of 40 is added for catalyzing, in which the volume ratio of the resting cell suspension to the maleic acid solution is 2:8.

* * * * *